US006949642B2

(12) United States Patent
Gao et al.

(10) Patent No.: US 6,949,642 B2
(45) Date of Patent: Sep. 27, 2005

(54) PRODUCTION OF TERTIARY AMINES BY REDUCTIVE AMINATION

(75) Inventors: Zhinong Gao, Monmouth Junction, NJ (US); Chien-Kuang Chen, Marlboro, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 208 days.

(21) Appl. No.: 10/121,014

(22) Filed: Apr. 11, 2002

(65) Prior Publication Data

US 2002/0169313 A1 Nov. 14, 2002

Related U.S. Application Data

(60) Provisional application No. 60/284,854, filed on Apr. 19, 2001.

(51) Int. Cl.[7] ............................................. C07D 243/14
(52) U.S. Cl. ....................................................... 540/569
(58) Field of Search ......................................... 540/569

(56) References Cited

U.S. PATENT DOCUMENTS 6,100,395 A     8/2000    Chen et al.
6,458,783 B1 * 10/2002   Ding et al. .................. 514/220

FOREIGN PATENT DOCUMENTS

PL            150857       11/1990

OTHER PUBLICATIONS de Villepin et al, "Etude par Spectrophotometrie Infrarouge des Interactions entre l'Eau et Quelques Acides Monocarboxyliques en Solution dans le Tetrachlorure de Carbone" Annales de Chemie, tome 1 (9–10), pp. 365–376 (1966). English Translation.*

Black and DiCesare Investigations into the Mechanism of the Titanium Isopropoxide Catalyzed Reductive Amination Reaction Book of Abstracts, 213 ACS National Meeting, San Francisco, Apr. 13–17. CHED–580 American Chemical Society: Wasington DC (1997).* de Villepin et al, "Etude par Spectrophotometrie Infrarouge des Interactions entre l'Eau et Quelques Acides Monocarboxyliques en Solution dans le Tetrachlorure de Carbone" Annales de Chemie, tome 1 (9–10), pp. 365–376 (1966).*

U.S. Provisional Application No. 60/115,587 (Chen et al) filed Jan. 12, 1999.*

Borg, G. et al. "One–pot asymmetric synthesis of *tert*–butanesulfinyl–protected amines from ketones by the in situ reduction of *tert*–butanesulfinyl ketimines"; Tetrahedron Letters, 40: 6709–6712 (1999).

Borg, G. et al. "Asymmetric synthesis of amines and a,a–disubstituted amino acids from tert–butanesulfinyl ketimines"; Book of Abstracts, 219th ACS National Meeting (2000) [Abstract].

Liu, G. et al. "Synthesis of Enantiomerically Pure *N–tert*–Butanesulfinyl Imines (*tert*–Butanesulfinimines) by the Direct Condensation of *tert*–Butanesulfinamide with Aldehydes and Ketones"; J. Org. Chem. 64: 1278–1284 (1999).

Loh, T. et al. "A Highly Stereoselective One–Pot Asymmetric Synthesis of Homoallylic Amines and Amino Acids From Aldehydes"; Tetrahedron Letters, 38(5): 865–868 (1997).

Pollard, C.B. et al. "The mechanism of the Leuckart reaction"; J. Org. Chem. 16: 661–672 (1951).

Elderfield, R.C. "Study of the synthesis of plasmochin by the reductive amination method with Raney nickel"; J. Am. Chem. Soc., 70: 40–44 (1948).

Form PCT/ISA/220 (Apr. 2002); International Search Report of PCT/US02/11942, filed Apr. 12, 2002; mailed Dec. 23, 2002.

* cited by examiner

*Primary Examiner*—Richard L. Raymond
*Assistant Examiner*—Zachary C. Tucker
(74) *Attorney, Agent, or Firm*—Suzanne E. Babajko; Deanna L. Baxam; Burton Rodney

(57) ABSTRACT

A process for the production of tertiary amines by reductive amination of carbonyl compounds with secondary amines in the presence of a water scavenger, preferably trifluoroacetic acid anhydride, is disclosed. This process has applications in the preparation of imidazole-containing benzodiazepines, which are inhibitors of farnesyl protein transferase.

28 Claims, No Drawings

PRODUCTION OF TERTIARY AMINES BY REDUCTIVE AMINATION

RELATED APPLICATIONS

This application claims benefit of U.S. Provisional application Ser. No. 60/284,854 filed Apr. 19, 2001, the contents of which are hereby incorporated by reference.

BACKGROUND OF THE INVENTION

The present invention concerns an improved process for the production of tertiary amines by reductive amination. This improved process can be applied to the preparation of imidazole-containing benzodiazepines, which are inhibitors of farnesyl protein transferase that find utility in the treatment of a variety of cancers and other diseases (Ding, C. Z.; Hunt, J. T.; Kim, S. -h.; Mitt, T.; Bhide, R.; Leftheris, K. WO 9730992; Chem. Abstr. 1998, 127, 278213).

A number of methods have been previously reported for the reductive amination of carbonyl compounds with secondary amines in the presence of a reducing agent. The reducing agents previously used include: zinc (Lockemann, G. DE 503113; Chem. Abstr. 1931, 25, 522), $H_2$/Pd(or Pt, Ni) (Emerson, W. S. Org. React. 1948, 4, 174; Schaus, J. M.; Huser, D. L.; Titus, R. D. Synth. Commun. 1990, 20, 3553), organoselenides, such as selenophenol (Fujimori, K.; Yoshimoto, H.; Oae, S. Tetrahedron Left. 1980, 21, 3385), $NaBH_4$ (Verardo, G.; Giumanini, A. G.; Strazzolini, P. Synth. Commun. 1994, 24, 609), and $NaCNBH_3$ (Lee, M.; Garbiras, B. J. Synth. Commun. 1994, 24, 3129). All these reducing agents are subject to one or more drawbacks. They are either toxic, or else they are not selective, with the result that a number of other reducible groups could be affected by side-reactions with these reagents. Reducing agents such as the organoselenides and $NaCNBH_3$ are highly toxic, while zinc, $NaBH_4$, and $H_2$ over Pt, Pd, or Ni, for example, suffer from poor selectivity. $NaBH(OAc)_3$ was subsequently introduced to address these problems (Abdel-Magid, A. F.; Carson, K. G.; Harris, B. D.; Maryanoff, C. A.; Shah, R. D. J. Org. Chem. 1996, 61, 3849) and this reagent was used in the preparation of the aforementioned imidazole-containing benzodiazepine compounds (Ding, C. Z.; Hunt, J. T.; Kim, S. -h.; Mitt, T.; Bhide, R.; Leftheris, K., WO 9730992; Chem. Abstr. 1998, 127, 278213). Although the desired products were obtained from 1 H-benzodiazepine starting materials, a large excess of aldehyde was required for a satisfactory conversion. In addition, expensive chromatographic separation of products was necessary, so that this method was not readily adaptable to large scale preparation.

Reduction of amines preformed from primary anilines and aldehydes to secondary amines with $Et_3SiH$/TFA has been previously reported (Kursanov, D. N.; Parnes, Z. N.; Loim, N. M. Synthesis 1974, 633; Loim, N. M. Bull. Acad. Sci. USSR, Div. Chem. Sci. 1968, 1345). Reduction of the preformed aminal from secondary amine and formaldehyde to give tertiary amine using $Et_3SiH$/TFA has also been disclosed (Beulshausen, T.; Groth, U.; Schoellkopf, U. Liebigs Ann. Chem. 1992, 523).

The process for the production of tertiary amines by reductive alkylation of a secondary amine using hydrosilane and Lewis acid is the subject of U.S. Pat. No. 6,100,395, to Chen et al., which is commonly owned with the invention described herein. Optimization of the patented process entailed the use of an extended reaction period in order to improve the quality of the product. In practice, this led to a relatively long cycle time, on the order of 80–90 hours.

SUMMARY OF THE INVENTION

This invention provides a more efficient process for the preparation of tertiary amines. The improved process finds one application in the preparation of imidazole-containing benzodiazepines, which are inhibitors of farnesyl protein transferase. The process of this invention involves reacting a secondary amine with a carbonyl compound in a reaction medium including an acid, thereby forming an iminium salt intermediate and water, with a substantial portion of the by-product water being taken up by a water scavenger which is also included in the reaction medium, and thereafter reducing the iminium salt with a reducing agent to produce the desired tertiary amine.

By performing the process of the invention in the presence of a water scavenger, the rate of reaction is dramatically increased, which, in turn, substantially improves the overall cycle time and cost of the operation. Compared with the synthesis described in U.S. Pat. No. 6,100,395, the reaction described herein is faster, makes more efficient use of reactants, and achieves higher yields of the desired tertiary amines.

DETAILED DESCRIPTION OF THE INVENTION

In its broadest aspect, the present invention provides a more efficient process for the preparation of tertiary amines (V) from secondary amines (I) and carbonyl compounds (II). The process involves reacting a secondary amine (I) with a carbonyl compound (II) in an acid-containing reaction medium, thereby forming an iminium salt intermediate (IV) and water; removing the water from the reaction mixture with a water scavenger; and reducing said iminium salt (IV) with a reducing agent to produce said tertiary amine (V).

As shown in Scheme 1, reductive amination is an equilibrium process leading to the formation of iminium salt (IV) via the dehydration of the aminal (III) before the reduction step. The water scavenger in this reaction functions to shift the equilibrium to the right, and facilitates formation of the iminium salt. As a supplemental benefit, near quantitative preparation of the iminium species, in advance of the introduction of the reducing agent, substantially eliminates costly competitive side reactions with the carbonyl compound.

Scheme 1

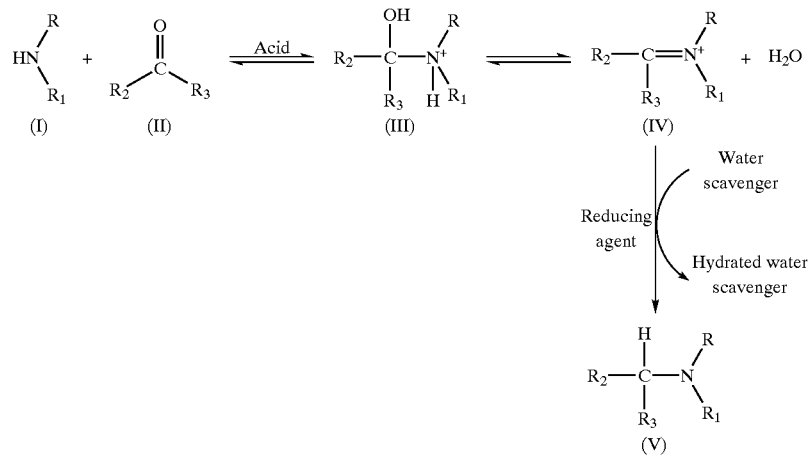

In a more preferred aspect, the present invention is concerned with the preparation of 1-substituted-2,3,4,5-tetrahydro-1,4-benzodiazepines (X) by the reaction of 1H-2,3,4,5-tetrahydro-1,4-benzodiazepine precursors (VI) with an aldehyde (VII) in the presence of an acid and a water scavenger, to produce an iminium species (IX) as an intermediate, which is then reduced to yield the desired product (Scheme 2).

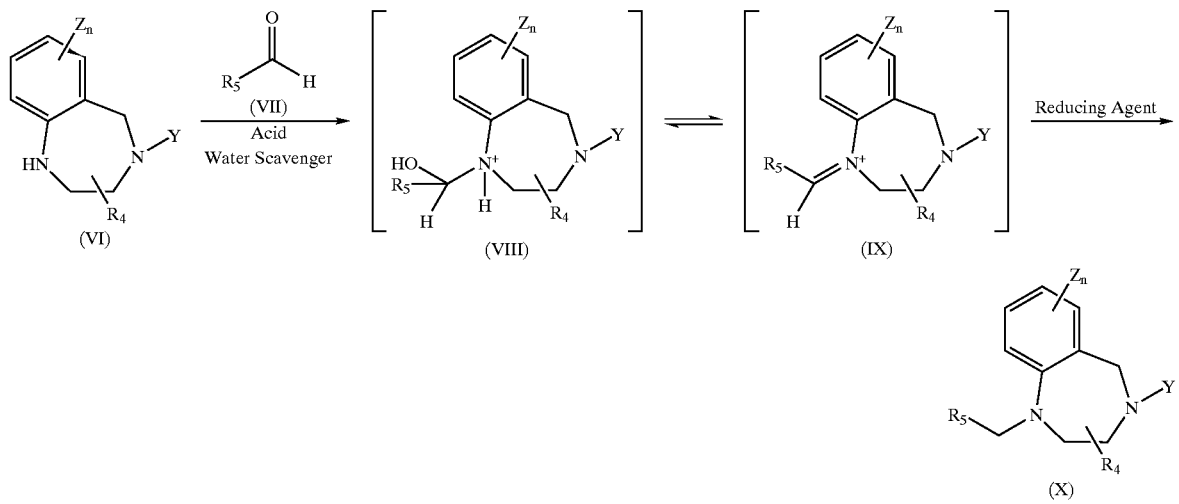

Generally speaking, for reactive amines and carbonyl compounds, a water scavenger is not required in a reductive amination, as the equilibrium normally favors the product. However, because 1H-2,3,4,5-tetrahydro-1,4-benzodiazepines and similar electron deficient secondary amines are not very reactive, a water scavenger facilitates reductive amination.

"Water scavenger" as use herein means any substance which removes or inactivates free water molecules, whether it be by a physical process such as absorption or adsorption, or by a chemical reaction.

Water scavengers suitable for use in the current invention include without limitation anhydrides of organic acids, aluminosilicates such as molecular sieves, other zeolites, finely divided silica gel, finely divided alumina, inorganic oxides such as barium oxide and calcium oxide, anhydrides of inorganic acids, such as phosphoric anhydride ($P_2O_5$), inorganic sulfates such as calcium sulfate, sodium sulfate, and magnesium sulfate, and other inorganic salts such as calcium chloride.

Preferred water scavengers are organic acid anhydrides and inorganic acid anhydrides.

Aggressive water scavengers such as trifluoroacetic acid anhydride and trichloroacetic acid anhydride are particularly preferred for use in the process of this invention.

In compounds I, II, III, IV, V, VI, VII, VIII, IX and X, above, the substituent groups R, $R_1$, $R_2$, $R_3$, $R_4$, and $R_5$ may be the same or different and represent hydrogen, $C_1$–$C_{12}$ alkyl groups, $C_1$–$C_{12}$ heteroalkyl groups, $C_5$–$C_{12}$ alkyl or heteroalkyl cyclic groups, $C_5$–$C_{30}$ aryl groups, $C_5$–$C_{30}$ heteroaryl groups, or $C_3$–$C_{30}$ groups with both saturated and unsaturated moieties, which groups may or may not be cyclic, and in which groups a heteroatom may optionally be substituted for one or more carbon atoms. Alternatively, R and $R_1$ taken together with the nitrogen to which they are attached may form a $C_5$–$C_{30}$ group which contains one or more cyclic moieties, which may contain one or more heteroatoms, and which may also contain both saturated and unsaturated moieties.

The Y substituent can be RC(O)—, ROC(O)—, $R_1R_2$NC(O)—, RS(O)$_2$—, ROS(O)$_2$— or $R_1R_2$NS(O)$_2$—, wherein R, $R_1$, and $R_2$ are as previously defined. The Z substituent represents hydrogen or at least one substituent selected from the group of halogen, RCOO—, RS(O)$_2$—, ROS(O)$_2$—, $R_1R_2$NS(O)$_2$—, —CN or —NO$_2$, wherein R, $R_1$, and $R_2$ are as previously defined, and n is an integer from 1–4. When n is greater than one, each Z substituent may be the same as or different from the other(s).

Suitable reducing agents for use in the above-described reactions include metal hydrides such as calcium hydride, lithium aluminum hydride, diborane, or sodium borohydride, alkylated metal hydrides such as trialkyltin hydrides, dialkyl aluminum hydrides, dialkyl boron hydrides, lithium triethyl borohydride, NaCNBH$_3$, or NaBH(OAc)$_3$, organoselenides such as selenophenol (PhSeH) and substituted selenophenols wherein the substituent or substituents are as described below for substituted alkyl groups, H$_2$ in conjunction with a catalytic metal such as palladium, platinum, or nickel, Raney nickel, and silanes of the formula SiH($R_aR_bR_c$) in which $R_a$, $R_b$ and $R_c$ independently represent $C_1$–$C_{12}$ alkyl or $C_2$–$C_{30}$ acyl.

Preferred reducing agents are H$_2$/Pd, silanes of the formula SiH($R_aR_bR_c$), NaCNBH$_3$, and NaBH(OAc)$_3$.

Silanes of the formula SiH($R_aR_bR_c$) are particularly preferred as the reducing agent for carrying out the process of the invention, as they are completely soluble in the reaction medium, as described below, and produce organic soluble by-products, thereby greatly facilitating work-up and isolation of the desired tertiary amines. The most preferred reducing agents are trialkylsilanes including triethylsilane and tri-iso-propylsilane.

Acids which may be used in the practice of this invention include protic acids and non-protic acids. Protic acids for use in the invention have a pK$_a$ within the range of about −2 to about 2.5. Representative examples of protic acids include acidic ion-exchange resins; inorganic acids such as HF, H$_2$SO$_3$, H$_3$PO$_4$, HNO$_2$; substituted sulfonic acids such as methanesulfonic acid, trifluoromethane sulfonic acid, o-aminobenzosulfonic acid, naphthalenesulfonic acid, and chlorosulfonic acid; organic carboxylic acids such as XCOOH wherein X is CH$_2$NO$_2$, monohalo-, dihalo-, or trihalo-substituted methyl, o-nitrophenyl, CN(CH$_2$)$_3$, CN(CH$_2$)$_2$, CNCH$_2$, o-(N$^+$(CH$_3$)$_3$)phenyl, 2,4,6-trihydroxyphenyl, and monohalo-, dihalo-, or trihalo-substituted acetyl; other organic acids such as maleic acid, lutidinic acid, oxalic acid quinolinic acid, dihydroxymalic acid, dihydroxytartaric acid, and cyclopropane-1,1-dicarboxylic acid; and acidic hydroxyls.

Representative examples of non-protic acids include metal halides such as titanium (IV) halides, zinc (II) halides, tin (IV) halides, aluminum (III) halides, and non-metal halides such as antimony (VI) halides, gallium (III) halides, and boron (III) halides.

Preferably, protic acids for use in the invention have a pK$_a$ in the range of about −0.3 to about 0.8. Preferred protic acids include halogenated alkanoic acids, such as trifluoroacetic acid and trichloroacetic acid, organic acids, such as trifluoromethane sulfonic acid, and naphthalene sulfonic acid, and acidic hydroxyls.

Preferred non-protic acids include titanium (IV) chloride, zinc (II) chloride, and boron trifluoride.

Particularly preferred acids for use in the current invention are trifluoroacetic acid, trichloroacetic acid, chlorosulfonic acid and the like. Trifluoroacetic acid is most preferred.

Suitable carbonyl compounds include, without limitation, ketones and aldehydes.

Preferred carbonyl compounds are aldehydes, including optionally substituted straight and branched-chain aliphatic aldehydes such as formaldehyde, acetaldehyde, propionaldehyde, butyraldehyde, valeraldehyde, caproaldehyde, heptaldehyde, or stearaldehyde, optionally substituted aromatic aldehydes such as benzaldehyde or salicylaldehyde, and optionally substituted heterocyclic aldehydes such as furfural, thiophene aldehyde, or imidazole carboxaldehydes, which include heterocyclic aldehydes of the formula VII-A

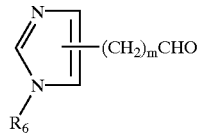

(VII-A)

wherein $R_6$ is H or lower alkyl and m is 1 or 2. More preferred are aldehydes of formula VII-A wherein $R_6$ is hydrogen or a methyl group. Most preferred are aldehydes of formula VII-A wherein $R_6$ is H and m is 1, i.e., imidazole-4-carboxaldehyde.

A preferred process for the preparation of 1-substituted-2,3,4,5-tetrahydro-1,4-benzodiazepines of formula X involves reaction of 1H-2,3,4,5-tetrahydro-1,4-benzodiazepine precursors of formula VI with an aldehyde of formula VII in the presence of trifluoroacetic acid as the acid and trifluoroacetic acid anhydride as the water scavenger, in a suitable solvent or solvent mixture, followed by reduction of the resulting iminium species of formula IX.

Suitable solvent(s) for use in the processes of the invention include, but are not limited to, hydrocarbons, halogenated hydrocarbons, ethers, esters, amides and nitriles. A preferred solvent is toluene. The reaction mixture temperature is preferably below about 30° C., more preferably below about 25° C.

Preferred compounds prepared by the process of the present invention are those of formula X-A (X-A)

[Structure diagram showing benzodiazepine with substituents Z, Y, R4, and imidazole-CH2 group with R6]

and salts, solvates, enantiomers and diastereomers thereof wherein

Z is Cl, Br, CN, optionally substituted phenyl or optionally substituted 2-, 3- or 4-pyridyl;

Y is $WR_7$;

$R_7$ is optionally substituted lower alkyl, optionally substituted aryl or optionally substituted heterocyclo;

$R_4$ is optionally substituted lower alkyl or optionally substituted aralkyl;

W is CO or $SO_2$; and $R_6$ is hydrogen or lower alkyl.

More preferred compounds of formula X-A which may be produced by the process of the present invention are those wherein Z is CN;

Y is $WR_7$;

$R_7$ is optionally substituted lower alkyl, optionally substituted phenyl, optionally substituted 2-thienyl, or optionally substituted 1-piperidinyl;

$R_4$ is optionally substituted benzyl;

W is CO or $SO_2$; and $R_6$ is hydrogen or methyl.

The most preferred compounds of formula X-A produced by the process of this invention are those wherein Z is CN;

Y is $WR_7$;

$R_7$ is n-propyl, n-butyl, 3-methoxypropyl, 2-thienyl, 5-bromo-2-thienyl, phenyl, 4-methoxyphenyl, or 1-piperidinyl;

$R_4$ is benzyl;

W is $SO_2$; and $R_6$ is hydrogen.

Representative compounds of formula X-A which may be prepared by the processes of this invention include (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile;

(R)-7-cyano-2,3,4,5-tetrahydro-1-(1H-imidazol-4-ylmethyl)-4-(1-oxobutyl)-3-(phenylmethyl)-1H-1,4-benzodiazepine;

(R)-4-[(5-bromo-2-thienyl)sulfonyl]-7-cyano-2,3,4,5-tetrahydro-1-(1H-imidazol-4-ylmethyl)-3-(phenylmethyl)-1H-1,4-benzodiazepine;

(R)-7-cyano-2,3,4,5-tetrahydro-1-(1H-imidazol-4-ylmethyl)-4-[(4-methoxyphenyl)sulfonyl]-3-(phenylmethyl)-1H-1,4-benzodiazepine;

(R)-7-cyano-2,3,4,5-tetrahydro-1-(1H-imidazol-4-ylmethyl)-3-(phenylmethyl)-4-(phenylsulfonyl)-1H-1,4-benzodiazepine;

(R)-7-cyano-2,3,4,5-tetrahydro-1-(1H-imidazol-4-ylmethyl)-3-(phenylmethyl)-4-(propylsulfonyl)-1H-1,4-benzodiazepine;

(R)-4-(butylsulfonyl)-7-cyano-2,3,4,5-tetrahydro-1-(1H-imidazol-4-ylmethyl)-3-(phenylmethyl)-1H-1,4-benzodiazepine;

(R)-7-cyano-2,3,4,5-tetrahydro-1-(1H-imidazol-4-ylmethyl)-3-(phenylmethyl)-4-(1-piperidinylsulfonyl)-1H-1,4-benzodiazepine; and (R)-4-(3-methoxypropylsulfonyl)-7-cyano-2,3,4,5-tetrahydro-1-(1H-imidazol-4-ylmethyl)-3-(phenylmethyl)-1H-1,4-benzodiazepine, among others.

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, 1 to 41 substituents, preferably 1 to 15 substituents, and most preferably one to four substituents. The substituents may include, without limitation, halo, trifluoromethyl, trifluoromethoxy, hydroxy, alkoxy, cycloalkoxy, heterocyclooxy, oxo, alkanoyl, aryloxy, alkanoyloxy, alkylamino, arylamino, aralkylamino, cycloalkylamino, heterocycloamino, optionally substituted amino, e.g. $NR_aR_b$, in which $R_a$ and $R_b$ is each independently selected from hydrogen, halogen, alkyl, alkoxy, aryl or aralkyl; alkanoylamino, aroylamino, aralkanoylamino, substituted alkanoylamino, substituted aroylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido, e.g. $SO_2NH_2$, substituted sulfonamido, e.g. $SO_2NR_aR_b$, nitro, cyano, carboxy, optionally substituted carbamyl, e.g. $CONR_aR_b$, where $R_a$ and $R_b$ are as defined above; alkoxycarbonyl, aryl, substituted aryl, guanidino and heterocyclos, such as indolyl, imidazolyl, furyl, thienyl, thiazolyl, pyrrolidyl, pyridyl, pyrimidyl and the like. Where it is noted above that the alkyl substituent is further substituted, it will be substituted with halogen, alkyl, alkoxy, aryl or aralkyl.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl moiety, such as benzyl. An aralkyl group may be substituted with any group described herein as an aryl or alkyl substitutent.

The term "substituted aryl" refers to an aryl group substituted by, for example, one to seven substituents, and, preferably, one to four substituents such as alkyl, substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The aryl group substituent may be further substituted by halo, hydroxy, alkyl, alkoxy, aryl, substituted aryl, substituted alkyl or aralkyl.

The term "cycloalkyl" refers to optionally substituted, saturated cyclic hydrocarbon ring systems, preferably containing 1 to 3 rings and 3 to 7 carbons per ring which may be further fused with an unsaturated $C_3$–$C_7$ carbocylic ring. Examples of cycloalkyl groups include cyclopropyl, cyclobutyl, cyclopentyl, cyclohexyl, cycloheptyl, cyclooctyl, cyclodecyl, cyclododecyl, and adamantyl. Examples of cycloalkyl group substituents include one or more alkyl groups as described above, or one or more groups described above as alkyl substituents.

The terms "heterocyclic", "heterocycle", and "heterocyclo" are used interchangeably herein to refer to an optionally substituted, fully saturated or unsaturated, aromatic or non-aromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2, 3, or 4 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Examples of monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydrothiopyranyl, tetrahydropyranyl, morpholinyl, thiamorpholinyl, thiamorpholinyl sulfoxide, tetrahydrothiopyranylsulfone, thiamorpholinyl sulfone, 1,3-dioxolane and tetrahydro-1,1-dioxothienyl, dioxanyl, isothiazolidinyl, thietanyl, thiiranyl, triazinyl, triazolyl, and the like, including the various isomeric forms thereof.

Examples of bicyclic hetrocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like, including the various isomeric forms thereof.

Examples of substituents for the foregoing heterocyclic groups include one or more alkyl groups as described above or one or more groups described above as alkyl substituents. Also included are smaller heterocyclos, such as epoxides and aziridines.

The term "heteroatoms" includes oxygen, sulfur and nitrogen.

The term "halogen" refers to F, Cl, Br, or I.

As used herein, the expression "optionally substituted," as in "optionally substituted lower alkyl", "optionally substituted aryl" or the like, refers to alkyl, aryl, and other groups which may be unsubstituted or substituted with the substituents mentioned above. Further, when a moiety is described herein as optionally substituted with more than one substituent, it is intended that each of the multiple substituents may be chosen independently from among the substituents mentioned above.

Compounds of formula X may form salts, which are also within the scope of this invention. Advantageously, pharmaceutically acceptable salts, that is, those which are non-toxic and physiologically compatible, such as methylsulfonates, hydrochlorides, hydrobromides and the like, may be formed by the addition of an acid to a solution comprising the formula X compound. Other salts may also be useful, e.g., in isolating or purifying the compounds made by the processes of the present invention.

The invention will now be further described by the following working examples, which are preferred embodiments of the invention. All temperatures are in degrees centigrade (° C.) unless otherwise indicated. These examples are provided for illustrative purposes only, and are in no way intended to limit the invention.

EXAMPLE I

Preparation of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile, X (R)-2,3,4,5-tetrahydro-3-(phenylmethyl)-4-(2-thienylsulfonyl)-1H-1,4-benzodiazepine-7-carbonitrile (10 g) and imidazole-4-carboxaldehyde (2.6 g) were mixed in toluene (20 mL) at 20 to 25° C. To this stirred slurry, first trifluoroacetic acid (9.4 mL) and then trifluoroacetic acid anhydride (5.2 mL) were added sequentially while maintaining the temperature below 30° C. The biphasic mixture was vigorously stirred at 20 to 25° C. for 2 hours. Triethylsilane was then added and the reaction mixture was stirred at 20 to 25° C. until the reaction was determined to be complete according to HPLC assay. The reaction mixture was polish-filtered, e.g., through filter paper or a celite bed. The solvent was removed by evaporation, and a viscous yellow oil containing approximately 100% yield of the crude title product was collected.

EXAMPLE II

Preparation of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile, mesylate salt The product of Example I was dissolved in anhydrous ethanol. The solution was heated to 60° C. Methanesulfonic acid was added at this temperature and a white slurry formed. The slurry was cooled to 0 to 5° C. over 1 hour and stirred for an additional 1 hour. The resulting white crystalline solid was filtered and washed with cold anhydrous ethanol. The wet cake was dried in a vacuum oven at 70° C. until the loss on drying (LOD) was <0.5% to afford the title product as a white, crystalline substance (13.2 g, 92.3% yield, HPLC AP >99). Typical yield is between about 92% to about 97%.

EXAMPLE III

Preparation of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile, X In a 500 mL flask was charged (R)-2,3,4,5-tetrahydro-3-(phenylmethyl)-4-(2-thienylsulfonyl)-1H-1,4-benzodiazepine-7-carbonitrile (25.0 g, 1 eq.), imidazole-4-carboxaldehyde (6.45 g, 1.1 eq.), and $CH_2Cl_2$ (150 mL) at room temperature. Cool to 0–5° C. Add trifluoroacetic acid (18.8 mL, 4 eq.) in a period of 10 min. A solution was obtained after addition. Stir the mixture for 10 min at 2° C. Add trichloroacetic acid anhydride (11.7 mL, 1.05 eq.) in a period of 20 min at 2° C. Stir the mixture for 30 min at 0–5° C. Add $Na(OAc)_3BH$ (15.51 g, 1.2 eq.) in two portions at 0–5° C. Agitate the mixture at 0° C. for 1.5 h, then room temperature for 1 hour. Add $CH_2Cl_2$ (100 mL), then cool to 0° C. Adjust the pH to 8–9 with 10% NaOH (about 125 mL used). Stir for 30 min. Separate the two phases. Wash the organic phase with $H_2O$ (2×100 mL), then separate the two phases. Remove most of the solvents, and add EtOH (200 mL); and heat up to 74° C. Stir for 10 min at 74° C. Cool to room temperature in a period of 60 min. Crystals appeared at 65° C. Filter and wash the crystals with EtOH (40 mL). Dry at 40° C. in vacuum oven over night to give the product (13.55 g, 90.7% yield) as a white solid.

EXAMPLE IV

Preparation of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile, mesylate salt Charge (R)-2,3,4,5-tetrahydro-3-(phenylmethyl)-4-(2-thienylsulfonyl)-1H-1,4-benzodiazepine-7-carbonitrile (30 g, 1 eq.) and imidazole-4-carboxaldehyde (7.8 g, 1.1 eq.) into 300 mL of $CH_2Cl_2$. Cool the mixture to 0–5° C., add trifluoroacetic acid (30 mL, 5 eq.), and follow with trifluoroacetic acid anhydride (15 mL, 1.5 eq.). Stir the solution at 0–5° C. for 15 min, then add a slurry of $Na(OAc)_3BH$ (21 g, 1.3 eq.) in 50 mL of $CH_2Cl_2$ while keeping the temperature below 20° C. Remove the ice-bath and stir the mixture at room temperature for 18 h. Cool the mixture to 0–5° C., adjust pH with 10% NaOH to 12.5 (ca. 250 mL used). Stir at room temperature for 30 min. Split the phases, and extract the aqueous phase with 50 mL of $CH_2Cl_2$. Wash the combined organic layer with 100 mL of water. Swap the $CH_2Cl_2$ to 300 mL of EtOH by distillation at normal pressure. Cool the solution to 20–25° C. over 1 h and stir for 30 min. Filter the slurry and wash the wet cake with 50 mL of EtOH. Transfer the wet cake to a 500-mL 3-neck flask, and add 300 mL of EtOH. Heat to reflux for 10 minutes. Slowly add methanesulfonic acid (4.8 mL). Keep stirring the clear solution at reflux for 30 min. Cool the mixture to room temperature over 1 h and stir at room temperature for 1 h. A slurry forms at 65° C. Filter the slurry and wash the cake with 50 mL of EtOH. Dry the cake at 40° C. in a vacuum oven overnight. The product is obtained as white solid (36.5 g, 84% yield).

EXAMPLE V

Preparation of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile, X In a 500 mL flask was charged (R)-2,3,4,5-tetrahydro-3-(phenylmethyl)-4-(2-thienylsulfonyl)-1H-1,4-benzodiazepine-7-carbonitrile (20.0 g, 1 eq.), imidazole-4-carboxaldehyde (5.2 g, 1.1 eq.), and $CH_2Cl_2$ (80 mL) at room temperature. Cool to 0–5° C. Add trichloroacetic acid (32 g, 4 eq.) and trichloroacetic acid anhydride (12.2 mL, 1.36 eq.) while keeping the temperature below 20° C. Stir the mixture for 30 min at 0–5° C. Add Triethylsilane (11.6 mL, 1.5 eq.). Agitate the mixture at 20–25° C. for 26 h until the reaction is complete. Add $CH_2Cl_2$ (80 mL), then cool to 0° C. Adjust the pH to 8–9 with 10% NaOH. Separate the two phases. Wash the organic phase with $H_2O$ (50 mL). Remove most of the solvents, and add EtOH (150 mL); and heat up to reflux and stir at reflux for 10 min. Cool to room temperature in a period of 60 min. Crystals appeared at 65° C. Stir at room temperature for 2 h. Filter and wash the crystals with EtOH (150 mL). Dry at 40° C. in vacuum oven over night to give the product (20.4 g, 85% yield) as a white solid.

What is claimed is:

1. A process for preparing a tertiary amine comprising
   (i) reacting a secondary amine which is a substituted or unsubstituted 1H-2,3,4,5-tetrahydro-1,4-benzodiazepine with a carbonyl compound in an acid-containing reaction medium, thereby forming an iminium salt intermediate and water, said reaction medium also including a water scavenger which removes free water molecules from the reaction mixture, and is selected from the group consisting of anhydrides of organic acids, acid chlorides, silica gel, alumina, aluminosilicates, inorganic oxides, anhydrides of inorganic acids and inorganic sulfates; and
   (ii) reducing said iminium salt with a reducing agent to produce said tertiary amine.

2. The process of claim 1 wherein said water scavenger is selected from anhydrides of organic acids and anhydrides of inorganic acids.

3. The process of claim 1 wherein said water scavenger is selected from the group consisting of trifluoroacetic acid anhydride and trichloroacetic acid anhydride.

4. The process of claim 1 wherein said reducing agent is selected from the group consisting of substituted or unsubstituted metal hydrides, substituted or unsubstituted organoselenides, $H_2$ in conjunction with a catalytic metal, and silanes.

5. The process of claim 1 wherein said reducing agent is selected from the group consisting of trialkylsilanes, $H_2$—Pd, $H_2$—Pt, $H_2$—Ni, substituted or unsubstituted organoselenides, $NaBH_4$, $NaCNBH_3$, and $NaBH(OAc)_3$.

6. The process of claim 1 wherein said reducing agent comprises a trialkylsilane.

7. The process of claim 1 wherein said reducing agent comprises triethylsilane or tri-iso-propylsilane.

8. The process of claim 1 wherein said carbonyl compound is selected from the group consisting of ketones and aldehydes.

9. The process of claim 1 wherein said carbonyl compound is an aldehyde.

10. The process of claim 1 wherein said carbonyl compound comprises imidazole-4-carboxaldehyde.

11. The process of claim 1 wherein said acid comprises a protic acid.

12. The process of claim 11 wherein said protic acid is selected from the group consisting of acidic ion-exchange resins, inorganic acids, substituted sulfonic acids, organic carboxylic acids, protonated heterocyclic compounds, and acidic hydroxyls.

13. The process of claim 11 wherein said protic acid is selected from the group consisting of trifluoroacetic acid, trichloroacetic acid, protonated o-chloropyridine, protonated diphenylamine, N-hydroxypyridine, trifluoromethane sulfonic acid and naphthalene sulfonic acid.

14. The process of claim 11 wherein said protic acid comprises trifluoroacetic acid or trifluoromethane sulfonic acid.

15. The process of claim 1 wherein said acid comprises a non-protic acid.

16. The process of claim 15 wherein said non-protic acid is selected from the group consisting of titanium (IV) halides, zinc (II) halides, tin (IV) halides, aluminum (III) halides, antimony (VI) halides, gallium (III) halides, and boron (III) halides.

17. The process of claim 15 wherein said non-protic acid comprises boron trifluoride.

18. The process of claim 1 wherein said reaction and reduction are carried out in a single reaction vessel.

19. The process of claim 1 wherein said secondary amine is a substituted or unsubstituted 1H-2,3,4,5-tetrahydro-1,4-benzodiazepine, said carbonyl compound comprises imidazole-4-carboxaldehyde, said reducing agent is triethylsilane, said water scavenger is trifluoroacetic acid anhydride, and said acid is trifluoroacetic acid.

20. A process for preparing a 1-substituted comprising
  (i) reacting a substituted or unsubstituted 1H-2,3,4,5-tetrahydro-1,4-benzodiazepine with an aldehyde in an acid-containing reaction medium, thereby forming a benzodiazepine iminium salt intermediate and water, said reaction medium also including a water scavenger which removes free water molecules which is selected from the group consisting of anhydrides of organic acids, acid chlorides, silica gel, alumina, aluminosilicates, inorganic oxides, anhydrides of inorganic acids and inorganic sulfates; and
  (ii) reducing said benzodiazepine iminium salt with a reducing age to produce said 1-substituted benzodiazepine.

21. The process of claim 20, wherein said water scavenger is trifluoroacetic acid anhydride.

22. The process of claim 20, wherein said substituted or unsubstituted benzodiazepine is (R)-1H-3-benzyl-4-(2-thienylsulfonyl)-7-cyano-2,3,4,5-tetrahydro-1,4-benzodiazepine.

23. The process of claim 20, wherein said aldehyde is imidazole-4-carboxaldehyde.

24. The process of claim 20, wherein said reducing agent is triethylsilane.

25. The process of claim 20, wherein said acid is trifluoroacetic acid.

26. The process of claim 20, wherein said reaction and reduction are carried out in a single reaction vessel.

27. A process for preparing (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile comprising
  (i) reacting (R)-2,3,4,5-tetrahydro-3-(phenylmethyl)-4-(2-thienylsulfonyl)-1H-1,4-benzodiazepine-7-carbonitrile with imidazole-4-carboxaldehyde in a reaction medium including trifluoroacetic acid, thereby forming a benzodiazepine iminium salt intermediate and water, said reaction medium also including trifluoroacetic acid anhydride; and
  (ii) reducing said benzodiazepine iminium salt with triethylsilane to produce said (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile.

28. The process of claim 27, wherein said reaction an reduction are carried out in a single reaction vessel.

* * * * *

UNITED STATES PATENT AND TRADEMARK OFFICE
CERTIFICATE OF CORRECTION

PATENT NO. : 6,949,642 B2
DATED : September 27, 2005
INVENTOR(S) : Zhinong Gao et al.

It is certified that error appears in the above-identified patent and that said Letters Patent is hereby corrected as shown below:

<u>Column 14,</u>
Line 1, after "substituted" and before "comprising", insert -- benzodiazepine --.
Line 48, change "reaction an" to -- reaction and --.

Signed and Sealed this

Twenty-ninth Day of November, 2005

JON W. DUDAS
*Director of the United States Patent and Trademark Office*